US008535896B2

(12) United States Patent
Schmiegel et al.

(10) Patent No.: US 8,535,896 B2
(45) Date of Patent: Sep. 17, 2013

(54) BIOMARKERS FOR INFLAMMATION OF THE LIVER

(75) Inventors: Wolff Schmiegel, Bochum (DE); Bence Sipos, Kiel (DE); Christian Mölleken, Bochum (DE); Günter Klöppel, Kiel (DE); Helmut E. Meyer, Recklinghausen (DE); Barbara Sitek, Bochum (DE); Kai Stühler, Köln (DE)

(73) Assignees: Wolff Schmiegel, Bochum (DE); Bence Sipos, Kiel (DE); Helmut E. Meyer, Recklinghausen (DE); Kai Stuhler, Köln (DE); Barbara Sitek, Bochum (DE)

( * ) Notice: Subject to any disclaimer, the term of this patent is extended or adjusted under 35 U.S.C. 154(b) by 1013 days.

(21) Appl. No.: 12/377,058

(22) PCT Filed: Aug. 10, 2007

(86) PCT No.: PCT/DE2007/001427
§ 371 (c)(1),
(2), (4) Date: Jun. 26, 2009

(87) PCT Pub. No.: WO2008/017303
PCT Pub. Date: Feb. 14, 2008

(65) Prior Publication Data
US 2010/0240545 A1  Sep. 23, 2010

(30) Foreign Application Priority Data

Aug. 10, 2006 (DE) .......................... 10 2006 037 613
Oct. 12, 2006 (DE) .......................... 10 2006 048 249

(51) Int. Cl.
*G01N 31/00* (2006.01)
*G01N 33/53* (2006.01)
(52) U.S. Cl.
USPC ........... 435/7.21; 435/7.1; 436/501; 436/518; 424/9.1; 530/300; 530/350
(58) Field of Classification Search
None
See application file for complete search history.

(56) References Cited

U.S. PATENT DOCUMENTS

| 2003/0152923 A1 | 8/2003 | Yakhini et al. |
| 2003/0228570 A1 | 12/2003 | Yat Wah Tom et al. |
| 2004/0157255 A1 | 8/2004 | Agus et al. |
| 2005/0136489 A1 | 6/2005 | Seng et al. |

FOREIGN PATENT DOCUMENTS

| EP | 1811041 | 7/2007 |
| WO | WO 03/022987 | 3/2003 |
| WO | WO 2006/019037 | 2/2006 |

OTHER PUBLICATIONS

Hirano et al. (European Journal of Biochemistry, vol. 234, No. 1, 1995).*
Morand et al. (The Journal of Biological Chemistry, vol. 280, pp. 17626-17633, May 6, 2005).*
Gourley, Glenn R. et al, "Proteomics to predict hepatitis C fibrosis", Hepatology, vol. 38, No. 4 Supplement 1, Oct. 2003, pp. 442A-443A.
Blanc, Jean-Frederic et al., "Proteomic analysis of differentially expressed proteins in hepatocellular carcinoma deloped in patients with chronic viral hepatisis C", Proteomics Sep. 2005, vol. 5, No. 14, Sep. 2005, pp. 3778-3789.
Shackel, N. et al., "Novel differential gene expression in human cirrhosis detected by suppression subtractive hydridization", Hepatology, Williams and Wilkins, Baltimore, MD, US, vol. 38, No. 3, Sep. 2003, pp. 577-588.
Smith, M. et al., "Hepatitis C virus and liver disease: Global transcriptional profiling and identification of potential markers", Hepatology, Williams and Wilkins, Baltimore, MD, US, vol. 38, No. 6, Dec. 2003, pp. 1458-1467.
Shackel, N. et al., "Insights into the pathobiology of hetatitis C virus-associated cirrhosis analysis of intrahepatic differential gene expression", American Journal of Pathology, Philadelphia, PA, US, vol. 160, No. 2, Feb. 2002, pp. 641-654.
Yun, Jing-Ping et al., "Nuclear matrix protein expressions in hepatocytes of normal and cirrhotic rat livers under normal and regenerating conditions", Journal of Cellular Biochemistry, vol. 91, No. 6, Apr. 15, 2004, pp. 1269-1279.
Kita et al., "Evidence for phophorylation of rat liver glucose-regulated protein 58, GRP58/ERp57/ER-60, indcued by fasting and leptin" Jan. 9, 2006, Febs Letters, Elsevier, Amsterdam, NL, pp. 199-205.
Hirano, N. et al., "Molecular cloning of the human glucose-regulated protsin ERP57/GRP58, a thioldependent reductase identification of its secretory form and inducible expression by the oncogenic transformation", European Journal of Biochemistry, Berlin, DE, vol. 234, No. 1, 1995, pp. 336-342.

(Continued)

*Primary Examiner* — Lisa Cook
(74) *Attorney, Agent, or Firm* — Novak Druce Connolly Bove + Quigg LLP (57) ABSTRACT

The invention relates to a method for the diagnostic investigation of biological samples from a person for inflammation of the liver, in particular hepatic fibrosis and/or cirrhosis of the liver, where the sample is investigated for one or more proteins as markers of inflammation of the liver, in particular hepatic fibrosis and/or cirrhosis of the liver, where a concentration of the proteins which is elevated or decreased by comparison with the healthy state indicates the presence of an inflammation of the liver, in particular a hepatic fibrosis and/or cirrhosis of the liver. The proteins are selected from the group of ER6Q, vimentin, actin alpha 1 skeletal muscle protein, hMFAP 4, tropomyosin, PTGES 2, amyloid P component, transgelin, calponin 1, *homo sapiens* p20 protein, 17 kDa myosin light chain, H chain H Igg B12, prolyl 4-hydroxylase, beta subunit methylenetetrahydrofolate dehydrogenase 1, PRO2619, aldehyde dehydrogenase 1, fibrinogen alpha chain preproprotein, fructose-bisphosphate aldolase B, argininosuccinate synthetase, Eefla2, AT P 5 A1, alpha-2 actin, regucalcin, serum albumin, mitochondrial malate dehydrogenase, mitochondrial acetoacetyl-CoA thiolase or in each case a partial sequence thereof.

14 Claims, 1 Drawing Sheet

(56) References Cited

OTHER PUBLICATIONS

Ueki, N., et al., "Induction of calponin-h1 by transforming growth factor-β1 in cultured human Ito cells, LI90", Biochimica et Biophysica Acta, vol. 1403, 1998, pp. 28-36.

Jiang, F. et al., "Gene expression profile of quiescent and activated rat hepatic stellate cells implicates Wnt signaling pathway in activation", Journal of Hepatology, vol. 45, 2006, pp. 401-409.

Huang, J., et al., "Correlation between genomic DNA copy number alterations and transcriptional expression in hepatitis B virus-associated hepatocellular carcinoma", FEBS Letters, vol. 580, 2006, pp. 3571-3581.

English Abstract from Espacenet.com of WO 2006/019037, Feb. 23, 2006.

* cited by examiner

SEQUENCE LISTING

<160> NUMBER OF SEQ ID NOS: 7

<210> SEQ ID NO 1
<211> LENGTH: 284
<212> TYPE: PRT
<213> ORGANISM: Homo sapiens

<400> SEQUENCE: 1

Met Asp Ala Ile Lys Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
            20                  25                  30

Glu Asp Arg Ser Lys Gln Leu Glu Glu Asp Ile Ala Ala Lys Glu Lys
        35                  40                  45

Leu Leu Arg Val Ser Glu Asp Glu Arg Asp Arg Val Leu Glu Glu Leu
    50                  55                  60

His Lys Ala Glu Asp Ser Leu Leu Ala Ala Glu Glu Ala Ala Ala Lys
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
    130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                165                 170                 175

Glu Arg Ala Glu Glu Arg Ala Glu Leu Ser Glu Gly Lys Cys Ala Glu
            180                 185                 190

Leu Glu Glu Glu Leu Lys Thr Val Thr Asn Asp Leu Lys Ser Leu Glu
        195                 200                 205

Ala Gln Ala Glu Lys Tyr Ser Gln Lys Glu Asp Arg Tyr Glu Glu Glu
    210                 215                 220

Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255

Glu Asp Glu Leu Tyr Ala Gln Lys Leu Lys Tyr Lys Ala Ile Ser Glu
            260                 265                 270

Glu Leu Asp His Ala Leu Asn Asp Met Thr Ser Ile
        275                 280

<210> SEQ ID NO 2
<211> LENGTH: 284
<212> TYPE: PRT
<213> ORGANISM: Homo sapiens

<400> SEQUENCE: 2

Met Asp Ala Ile Lys Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
            20                  25                  30

```
Glu Asp Arg Ser Lys Gln Leu Glu Glu Asp Ile Ala Ala Lys Glu Lys
             35                  40                  45

Leu Leu Arg Val Ser Glu Asp Arg Asp Arg Val Leu Glu Glu Leu
 50                  55                  60

His Lys Ala Glu Asp Ser Leu Leu Ala Ala Glu Glu Ala Ala Lys
 65                  70                  75                  80

Ala Glu Ala Asp Val Ala Ser Leu Asn Arg Arg Ile Gln Leu Val Glu
                     85                  90                  95

Glu Glu Leu Asp Arg Ala Gln Glu Arg Leu Ala Thr Ala Leu Gln Lys
                    100                 105                 110

Leu Glu Glu Ala Glu Lys Ala Ala Asp Glu Ser Glu Arg Gly Met Lys
                    115                 120                 125

Val Ile Glu Ser Arg Ala Gln Lys Asp Glu Glu Lys Met Glu Ile Gln
130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                    165                 170                 175

Glu Arg Ala Glu Glu Arg Ala Glu Leu Ser Glu Gly Lys Cys Ala Glu
                    180                 185                 190

Leu Glu Glu Glu Leu Lys Thr Val Thr Asn Asp Leu Lys Ser Leu Glu
                    195                 200                 205

Ala Gln Ala Glu Lys Tyr Ser Gln Lys Glu Asp Arg Tyr Glu Glu Glu
                    210                 215                 220

Ile Lys Val Leu Ser Asp Lys Leu Lys Ala Glu Thr Arg Ala Glu
225                 230                 235                 240

Phe Ala Glu Arg Ser Val Thr Lys Leu Glu Lys Ser Ile Asp Asp Leu
                    245                 250                 255

Glu Asp Glu Leu Tyr Ala Gln Lys Leu Lys Tyr Lys Ala Ile Ser Glu
                    260                 265                 270

Glu Leu Asp His Ala Leu Asn Asp Met Thr Ser Ile
                    275                 280

<210> SEQ ID NO 3
<211> LENGTH: 284
<212> TYPE: PRT
<213> ORGANISM: Homo sapiens

<400> SEQUENCE: 3

Met Asp Ala Ile Lys Lys Lys Met Gln Met Leu Lys Leu Asp Lys Glu
 1               5                  10                  15

Asn Ala Ile Asp Arg Ala Glu Gln Ala Glu Ala Asp Lys Lys Gln Ala
                 20                  25                  30

Glu Asp Arg Cys Lys Gln Leu Glu Glu Glu Gln Ala Leu Gln Lys
             35                  40                  45

Lys Leu Lys Gly Thr Glu Asp Glu Val Glu Lys Tyr Ser Glu Ser Val
 50                  55                  60

Lys Glu Ala Gln Glu Lys Leu Glu Gln Ala Glu Lys Ala Thr Asp
 65                  70                  75                  80

Ala Glu Ala Asp Val Ala Ser Leu Asn Arg Arg Ile Gln Leu Val Glu
                     85                  90                  95

Glu Glu Leu Asp Arg Ala Gln Glu Arg Leu Ala Thr Ala Leu Gln Lys
                    100                 105                 110

Leu Glu Glu Ala Glu Lys Ala Ala Asp Glu Ser Glu Arg Gly Met Lys
                    115                 120                 125
```

```
Val Ile Glu Asn Arg Ala Met Lys Asp Glu Lys Met Glu Leu Gln
        130                 135                 140

Glu Met Gln Leu Lys Glu Ala Lys His Ile Ala Glu Asp Ser Asp Arg
145                 150                 155                 160

Lys Tyr Glu Glu Val Ala Arg Lys Leu Val Ile Leu Glu Gly Glu Leu
                165                 170                 175

Glu Arg Ser Glu Glu Arg Ala Glu Val Ala Glu Ser Arg Ala Arg Gln
                180                 185                 190

Leu Glu Glu Glu Leu Arg Thr Met Asp Gln Ala Leu Lys Ser Leu Met
            195                 200                 205

Ala Ser Glu Glu Glu Tyr Ser Thr Lys Glu Asp Lys Tyr Glu Glu Glu
        210                 215                 220

Ile Lys Leu Leu Glu Glu Lys Leu Lys Glu Ala Glu Thr Arg Ala Glu
225                 230                 235                 240

Phe Ala Glu Arg Ser Val Ala Lys Leu Glu Lys Thr Ile Asp Asp Leu
                245                 250                 255

Glu Glu Thr Leu Ala Ser Ala Lys Glu Glu Asn Val Glu Ile His Gln
            260                 265                 270

Thr Leu Asp Gln Thr Leu Leu Glu Leu Asn Asn Leu
            275                 280

<210> SEQ ID NO 4
<211> LENGTH: 284
<212> TYPE: PRT
<213> ORGANISM: Homo sapiens

<400> SEQUENCE: 4

Met Asp Ala Ile Lys Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
            20                  25                  30

Glu Asp Arg Ser Lys Gln Leu Glu Asp Glu Leu Val Ser Leu Gln Lys
        35                  40                  45

Lys Leu Lys Gly Thr Glu Asp Glu Leu Asp Lys Tyr Ser Glu Ala Leu
50                  55                  60

Lys Asp Ala Gln Glu Lys Leu Glu Leu Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                165                 170                 175

Glu Arg Ala Glu Glu Arg Ala Glu Leu Ser Glu Gly Gln Val Arg Gln
                180                 185                 190

Leu Glu Glu Gln Leu Arg Ile Met Asp Gln Thr Leu Lys Ala Leu Met
            195                 200                 205

Ala Ala Glu Asp Lys Tyr Ser Gln Lys Glu Asp Arg Tyr Glu Glu Glu
        210                 215                 220
```

```
Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255

Glu Glu Lys Val Ala His Ala Lys Glu Glu Asn Leu Ser Met His Gln
                260                 265                 270

Met Leu Asp Gln Thr Leu Leu Glu Leu Asn Asn Met
                275                 280
```

<210> SEQ ID NO 5
<211> LENGTH: 248
<212> TYPE: PRT
<213> ORGANISM: Homo sapiens
<400> SEQUENCE: 5

```
Met Ala Gly Leu Asn Ser Leu Glu Ala Val Lys Arg Lys Ile Gln Ala
1               5                   10                  15

Leu Gln Gln Gln Ala Asp Glu Ala Glu Asp Arg Ala Gln Gly Leu Gln
                20                  25                  30

Arg Glu Leu Asp Gly Glu Arg Glu Arg Arg Glu Lys Ala Glu Gly Asp
            35                  40                  45

Val Ala Ala Leu Asn Arg Arg Ile Gln Leu Phe Glu Glu Glu Leu Asp
50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Met Lys Asp Glu Glu Lys Met Glu Ile Gln Glu Met Gln Leu
            100                 105                 110

Lys Glu Ala Lys His Ile Ala Glu Glu Ala Asp Arg Lys Tyr Glu Glu
            115                 120                 125

Val Ala Arg Lys Leu Val Ile Leu Glu Gly Glu Leu Glu Arg Ala Glu
            130                 135                 140

Glu Arg Ala Glu Val Ser Glu Leu Lys Cys Gly Asp Leu Glu Glu Glu
145                 150                 155                 160

Leu Lys Asn Val Thr Asn Asn Leu Lys Ser Leu Glu Ala Ala Ser Glu
                165                 170                 175

Lys Tyr Ser Glu Lys Glu Asp Lys Tyr Glu Glu Ile Lys Leu Leu
            180                 185                 190

Ser Asp Lys Leu Lys Glu Ala Glu Thr Arg Ala Glu Phe Ala Glu Arg
            195                 200                 205

Thr Val Ala Lys Leu Glu Lys Thr Ile Asp Asp Leu Glu Glu Lys Leu
210                 215                 220

Ala Gln Ala Lys Glu Glu Asn Val Gly Leu His Gln Thr Leu Asp Gln
225                 230                 235                 240

Thr Leu Asn Glu Leu Asn Cys Ile
                245
```

<210> SEQ ID NO 6
<211> LENGTH: 201
<212> TYPE: PRT
<213> ORGANISM: Homo sapiens
<400> SEQUENCE: 6

```
Met Ala Asn Lys Gly Pro Ser Tyr Gly Met Ser Arg Glu Val Gln Ser
1               5                   10                  15

Lys Ile Glu Lys Lys Tyr Asp Glu Glu Leu Glu Glu Arg Leu Val Glu
```

-continued

```
                    20                  25                  30

Trp Ile Ile Val Gln Cys Gly Pro Asp Val Gly Arg Pro Asp Arg Gly
            35                  40                  45

Arg Leu Gly Phe Gln Val Trp Leu Lys Asn Gly Val Ile Leu Ser Lys
        50                  55                  60

Leu Val Asn Ser Leu Tyr Pro Asp Gly Ser Lys Pro Val Lys Val Pro
 65                  70                  75                  80

Glu Asn Pro Pro Ser Met Val Phe Lys Gln Met Glu Gln Val Ala Gln
                85                  90                  95

Phe Leu Lys Ala Ala Glu Asp Tyr Gly Val Ile Lys Thr Asp Met Phe
            100                 105                 110

Gln Thr Val Asp Leu Phe Glu Gly Lys Asp Met Ala Ala Val Gln Arg
        115                 120                 125

Thr Leu Met Ala Leu Gly Ser Leu Ala Val Thr Lys Asn Asp Gly His
130                 135                 140

Tyr Arg Gly Asp Pro Asn Trp Phe Met Lys Lys Ala Gln Glu His Lys
145                 150                 155                 160

Arg Glu Phe Thr Glu Ser Gln Leu Gln Glu Gly Lys His Val Ile Gly
                165                 170                 175

Leu Gln Met Gly Ser Asn Arg Gly Ala Ser Gln Ala Gly Met Thr Gly
            180                 185                 190

Tyr Gly Arg Pro Arg Gln Ile Ile Ser
        195                 200
```

<210> SEQ ID NO 7
<211> LENGTH: 184
<212> TYPE: PRT
<213> ORGANISM: Homo sapiens

<400> SEQUENCE: 7

```
Met Ala Asn Lys Gly Pro Ser Tyr Gly Met Ser Arg Glu Val Gln Ser
 1               5                  10                  15

Lys Ile Glu Lys Lys Tyr Asp Glu Glu Leu Glu Glu Arg Leu Val Glu
                20                  25                  30

Trp Ile Ile Val Gln Arg Gly Pro Asp Val Gly Arg Pro Asp Arg Gly
            35                  40                  45

Arg Leu Gly Phe Gln Val Trp Leu Lys Asn Gly Val Ile Leu Ser Lys
        50                  55                  60

Leu Val Asn Ser Leu Tyr Pro Asp Gly Ser Lys Pro Val Lys Val Pro
 65                  70                  75                  80

Glu Asn Pro Pro Ser Met Val Phe Lys Gln Met Glu Gln Val Ala Gln
                85                  90                  95

Phe Leu Lys Ala Ala Glu Asp Tyr Gly Val Ile Lys Thr Asp Met Phe
            100                 105                 110

Gln Thr Val Asp Leu Phe Glu Gly Lys Asp Met Ala Ala Val Gln Arg
        115                 120                 125

Thr Leu Met Ala Leu Gly Ser Leu Ala Val Thr Lys Asn Asp Gly His
130                 135                 140

Tyr Arg Gly Asp Pro Asn Trp Phe Met Lys Lys Ala Gln Glu His Lys
145                 150                 155                 160

Arg Glu Phe Thr Glu Ser Gln Leu Gln Glu Gly Lys His Val Ile Gly
                165                 170                 175

Leu Gln Met Gly Ser Asn Arg Gly
            180
```

BIOMARKERS FOR INFLAMMATION OF THE LIVER

RELATED APPLICATIONS

This application is a national stage application (under 35 U.S.C. §371) of PCT/DE2007/001427, filed Aug. 10, 2007, which claims benefit of German application 102006037613.7, filed Aug. 10, 2006 and German application 102006048249.2, filed Oct. 12, 2006.

DESCRIPTION

The invention relates to a method for the diagnostic study of biological samples of a human for inflammation of the liver, in particular hepatic fibrosis and/or cirrhosis of the liver, the sample being studied for one or more proteins as a marker for inflammation of the liver, in particular hepatic fibrosis and/or cirrhosis of the liver, a concentration of the proteins which is elevated or decreased in relation to the healthy state indicating the presence of an inflammation of the liver, in particular a hepatic fibrosis and/or cirrhosis of the liver.

Approximately 170 million humans are chronically infected with the hepatitis C virus (HCV) worldwide. The course of the illness varies significantly between the patients; while approximately 20% of the patients develop cirrhosis of the liver within 20 years, in other patients, a development of this type is not to be observed even after still longer periods of time. An array of factors may be identified which increase the probability of a hepatic fibrosis and/or cirrhosis of the liver, inter alia, male sex, alcohol misuse, co-infection with HIV or *Schistosoma mansoni*, genetic predisposition, and advanced age upon the infection.

Above all, the hepatic stellate cells (HSC), which are responsible in a normal liver in the rest state for the storage of vitamin A in particular, are responsible for the development of a liver fibrosis and/or cirrhosis of the liver. In contrast, in a fibrotic liver, they are activated, proliferate, and develop into myofibroblastic cells. These myofibroblasts produce large quantities of collagen, down-regulate the production of matrix metalloproteinases (MMP), and display an increased expression of the physiological inhibitors of the MMP (TIMP). With increasing collagen accumulation, the fibrosis of the liver develops further, which finally may result in organ failure.

In particular peg-interferon alpha and ribavirin are used for the antiviral treatment of chronic hepatitis C. Although many patients may be successfully treated in this way, the therapy remains unsuccessful in at least 50% of the patients, who are infected with the HCV genotype 1, which is the most widespread in the Western world. This is similarly true for patients who are infected with the HCV genotype 4, which frequently occurs in Egypt. In addition, the costs of permanent antiviral treatment are immense and the treatment is connected with significant side effects. In patients who are in a significantly advanced stage, the antiviral treatment again no longer results in the desired success. Therefore, there is a need to be able to better diagnose a fibrosis in hepatitis patients and thus the occurrence of cirrhosis of the liver, to be able to provide the treating physician with the capability of deciding whether an antiviral treatment is advisable and promising.

An array of noninvasive markers has already been used in the past for the detection of liver fibrosis, among them the so-called acti-test or fibro-test, pro-collagen III-peptide (PIIIP), hyaluronic acid, matrix metalloproteinases (MMP) and their inhibitors (TIMP) (T. Poynard et al., *Expert Rev Mol Diagn.* 2005, 5 (1): 15-21; V. Leroy et al., *J Hep* 2001, 35 (1):26). However, all of these markers only show a limited sensitivity and specificity, because of which there is a further demand for more suitable biomarkers.

Proceeding from the described prior art, the object therefore presents itself of providing an improved method for studying biological samples for inflammation of the liver and/or hepatic fibrosis and/or cirrhosis of the liver, in which novel markers are used.

The object is achieved according to the invention by a method for studying biological samples of a human for inflammation of the liver, in particular hepatic fibrosis and/or cirrhosis of the liver, the sample being studied for one or more proteins as a marker for an inflammation of the liver, in particular hepatic fibrosis and/or cirrhosis of the liver, and an elevated level of the proteins indicating the presence of an inflammation of the liver, in particular hepatic fibrosis and/or cirrhosis of the liver, the proteins being selected from a group comprising: ER60, vimentin, actin alpha 1 skeletal muscle protein, hMFAP4, tropomyosin, PTGES2, amyloid-P-component, transgelin, calponin 1, *Homo sapiens* p20 protein, 17 kDa myosin light chain, H chain H IgG B12, prolyl 4-hydroxylase, beta subunit.

Furthermore, the invention also relates to a corresponding method in which a decreased level of the proteins indicates the presence of an inflammation of the liver, in particular hepatic fibrosis and/or cirrhosis of the liver, in this case the proteins being selected from a group: methylene tetrahydrofolate dehydrogenase 1, PRO2619, aldehyde dehydrogenase 1, fibrinogen alpha-chain preproprotein, fructose-bisphosphate-aldolase B, argininosuccinate synthetase, EEF1A2, ATP5A1, alpha-2-actin, regucalcin, serum albumin, mitochondrial malate dehydrogenase, mitochondrial acetoacetyl-CoA thiolase.

Both for the up-regulating and also for the down-regulating proteins, the study may also be performed via the determination of partial sequences of the biomarkers (also: marker proteins) according to the invention. In particular, such partial sequences preferably comprise 60% of the amino acid sequence of a biomarker according to the invention, in particular 70% and more, 80% and more, in particular 90 to 95%.

In the context of this invention, the term inflammation of the liver comprises any form of hepatitis, but particularly hepatic fibrosis up to cirrhosis of the liver (on the terms, please see the relevant Pschyrembel, Klinisches Wörterbuch [Clinical Dictionary], 260th edition, 2004, Berlin, for example). Hepatic fibrosis and cirrhosis of the liver are preferred according to the invention.

Furthermore, the invention also relates to the diagnosis of inflammation of the liver, in particular hepatic fibrosis and/or cirrhosis of the liver, a determination of at least one protein selected from the group comprising: ER60, vimentin, actin alpha 1 skeletal muscle protein, hMFAP 4, tropomyosin, PTGES 2, amyloid-P-component, transgelin, calponin 1, *Homo sapiens* p20 protein, 17 kDa myosin light chain, H chain H IgG B12, prolyl 4-hydroxylase, beta subunit, methylene tetrahydrofolate dehydrogenase 1, PRO2619, aldehyde dehydrogenase 1, fibrinogen alpha-chain preproprotein, fructose bisphosphate aldolase B, argininosuccinate synthetase, EEF1A2, ATP5A1, alpha-2-actin, regucalcin, serum albumin, mitochondrial malate dehydrogenase, mitochondrial acetoacetyl-CoA thiolase, or a partial sequence thereof in each case being performed on a patient to be studied.

Furthermore, a combination of such biomarkers and/or marker proteins according to the invention is possible for the diagnosis according to the invention.

The cited proteins may be identified as potential biomarkers during a proteome analysis of fibrotic tissue in comparison to non-fibrotic tissue. For this purpose, liver biopsy samples were taken from patients infected with hepatitis C. The samples were homogenized with lysis buffer in a manual homogenizer and freed of DNA and other cell material to obtain a protein concentrate. The proteins were labeled using a pigment and subjected to a 2-D polyacrylamide gel electrophoresis using isoelectric focusing in the first dimension and SDS gel electrophoresis in the second dimension. The results were compared for fibrotic and non-fibrotic cells with the aid of software suitable for this purpose, to detect and quantify the spots which were amplified or decreased in the fibrotic sample in comparison to the non-fibrotic sample. For example, the ImageQuant™ software from GE Healthcare in connection with the DeCyder software of the same firm may be executed as the software. The emission of the pigments, using which the proteins were labeled, was measured and analyzed.

The further analysis was performed with the aid of LC-ESI-MS (liquid chromatography-electrospray ionization-mass spectrometry). Firstly the proteins were decomposed into individual peptide fragments with the aid of trypsin in the gel in which the samples had previously been separated. These fragments were separated from one another with the aid of reversed phase HPLC and studied using mass spectrometry to identify the individual proteins. Of course, other suitable mass spectrometry methods may also be applied for this purpose, such as MALDI-TOF-MS.

The following proteins were able to be identified in the studies, which were up-regulated (fold change positive) or down-regulated (fold change negative) in fibrotic cells in relation to non-fibrotic cells:

Up-Regulated Proteins

| NCBI accession | Identified protein | Fold change |
| --- | --- | --- |
| IPI00025252.1 | ER60 protein | 26.9 |
| IPI00418471.5 | vimentin | 5.6 |
| IPI00448938.1 | H chain H IgG B12 | 14.7 |
| IPI00697648.1 | actin alpha 1 skeletal muscle protein | 6.5 |
| IPI00022792.3 | hMFAP 4 | 45.1 |
| IPI00455050.1 | sarcomere tropomyosin kappa | 87.1 |
| IPI00014581.1 | TPM1 human tropomyosin alpha-chain | 28.7 |
| IPI00220709.3 | beta tropomyosin | 52.4 |
| IPI00010779.3 | tropomyosin 4 | 20.6 |
| IPI00303568.3 | PTGES 2 | 6.1 |
| IPI00010796.1 | prolyl 4-hydroxylase, beta subunit | 4.6 |
| IPI00022391.1 | amyloid P-component, serum | 7.3 |
| IPI00216138.5 | transgelin | 15 |
| IPI00021264.1 | calponin 1 | 21.1 |
| IPI00022433.5 | Homo sapiens p 20 protein [pir B53814] | 16.9 |
| IPI00718271.2 | 17 kDa myosin light chain | 8.4 |

Down-Regulated Proteins

| NCBI accession | Identified protein | Fold change |
| --- | --- | --- |
| IPI00218342.9 | methylene tetrahydrofolate dehydrogenase 1 | −9.37 |
| IPI00745872.1 | PRO2619 | −3.2 |
| IPI00218914.4 | aldehyde dehydrogenase 1 | −7.7 |
| IPI00029717.1 | fibrinogen alpha-chain preprotein | −6.4 |
| IPI00218407.5 | fructose bisphosphate aldolase B | −16.6 |
| IPI00020632.4 | argininosuccinate synthetase | −11.0 |
| IPI00014424.1 | EEF1A2 | −6.4 |
| IPI00440493.2 | ATP5A1 | −5.8 |
| IPI00708487.1 | alpha-2-actin; alpha cardiac actin | −8.6 |
| IPI00017551.1 | regucalcin (senescence marker protein 30) | −13.3 |
| IPI00708398.1 | ABBOS-serum albumin precursor | −13.3 |
| IPI00291006.1 | mitochondrial malate dehydrogenase precursor | −5.9 |
| IPI00030363.1 | mitochondrial acetoacetyl-CoA thiolase precursor | −5.9 |

NCBI: National Center for Biotechnology Information

The sequence information for several of the identified proteins is specified hereafter. The peptide sequences which, on the one hand, resulted in identification of the proteins and, on the other hand, permit a differentiation of the protein isoforms (compare also sequence listing as the appendix to the patent application), have a dark underlay.

Tropomyosin

SEQ ID NO 1
MDAIKKKMQMLKLDKENALDRAEQAEADKKAAEDRSKQLEEDIAAKEKLL

SEQ ID NO 2
MDAIKKKMQMLKLDKENALDRAEQAEADKKAAEDRSKQLEEDIAAKEKLL

SEQ ID NO 3
MDAIKKKMQMLKLDKENALDRAEQAEADKKQAEDRSKQLEEEQQALQKKL

SEQ ID NO 4
MDAIKKKMQMLKLDKENALDRAEQAEADKKAAEDRSKQLEDELVSLQKKL

SEQ ID NO 5
----------------------------------------MAGLNSLEAVKR
KI

SEQ ID NO 1
RVSEDERDRVLEELHKAEDSLLAAEEAAAKAEADVASLNRRIQLVEEELD

SEQ ID NO 2
RVSEDERDRVLEELHKAEDSLLAAEEAAAKAEADVASLNRRIQLVEEELD

SEQ ID NO 3
KGTEDEVEKYSESVKEAQEKLEQAEKKATDAEADVASLNRRIQLVEEELD

SEQ ID NO 4
KGTEDELDKYSEALKDAQEKLELAEKKATDAEADVASLNRRIQLVEEELD

SEQ ID NO 5
QALQQQADEAEDRAQGLQRELDGERERREKAEGDVAALNRRIQLFEEELD

SEQ ID NO 1
RAQERLATALQKLEEAEKAADESERGMKVIESRAQKDEEKMEIQEIQLKE

SEQ ID NO 2
RAQERLATALQKLEEAEKAADESERGMKVIESRAQKDEEKMEIQEIQLKE

SEQ ID NO 3
RAQERLATALQKLEEAEKAADESERGMKVIENRAMKDEEKMELQEMQLKE

SEQ ID NO 4
RAQERLATALQKLEEAEKAADESERGMKVIESRAQKDEEKMEIQEIQLKE

```
                                               SEQ ID NO 5
RAQERLATALQKLEEAEKAADESERGMKVIENRAMKDEEKMEIQEMQLKE

SEQ ID NO 1
AKHIAEDADRKYEEVARKLVIIESDLERAEERAELSEGKCAELEEELKTV

SEQ ID NO 2
AKHIAEDADRKYEEVARKLVIIESDLERAEERAELSEGKCAELEEELKTV

SEQ ID NO 3
AKHIAEDSDRKYEEVARKLVILEGELERSEERAEVAESRARQLEEELRTM

SEQ ID NO 4
AKHIAEDADRKYEEVARKLVIIESDLERAEERAELSEGQVRQLEEQLRIM

SEQ ID NO 5
AKHIAEEADRKYEEVARKLVILEGELERAEERAEVSELKCGDLEEELKNV

SEQ ID NO 1
TNDLKSLEAQAEKYSQKEDRYEEEIKVLSDKLKEAETRAEFAERSVTKLE

SEQ ID NO 2
TNDLKSLEAQAEKYSQKEDRYEEEIKVLSDKLKEAETRAEFAERSVTKLE

SEQ ID NO 3
DQALKSLMASEEEYSTKEDKYEEEIKLLEEKLKEAETRAEFAERSVAKLE

SEQ ID NO 4
DQTLKALMAAEDKYSQKEDR'YEEEIKVLSDKLKEAETRAEFAERSVTKL
E

SEQ ID NO 5
TNNLKSLEAASEKYSEKEDKYEEEIKLLSDKLKEAETRAEFAERTVAKLE

SEQ ID NO 1
KSIDDLEDELYAQKLKYKAISEELDHALNDMTSI

SEQ ID NO 2
KSIDDLEDELYAQKLKYKAISEELDHALNDMTSI

SEQ ID NO 3
KTIDDLEETLASAKEENVEIHQTLDQTLLELNNL

SEQ ID NO 4
KSIDDLEEKVAHAKEENLSMHQMLDQTLLELNNM

SEQ ID NO 5
KTIDDLEEKLAQAKEENVGLHQTLDQTLNELNCI

Transgelin
                                               SEQ ID NO 6
MANKGPSYGMSREVQSKIEKKYDEELEERLVEWIIVQCGPDVGRPDRGRL

SEQ ID NO 7
MANKGPSYGMSREVQSKIEKKYDEELEERLVEWIIVQRGPDVGRPDRGRL

SEQ ID NO 6
GFQVWLKNGVILSKLVNSLYPDGSKPVKVPENPPSMVFKQMEQVAQFLKA

SEQ ID NO 7
GFQVWLKNGVILSKLVNSLYPDGSKPVKVPENPPSMVFKQMEQVAQFLKA

SEQ ID NO 6
AEDYGVIKTDMFQTVDLFEGKDMAAVQRTLMALGSLAVTKNDGHYRGDPN

SEQ ID NO 7
AEDYGVIKTDMFQTVDLFEGKDMAAVQRTLMALGSLAVTKNDGHYRGDPN

SEQ ID NO 6
WFMKKAQEHKREFTESQLQEGKHVIGLQMGSNRGASQAGMTGYGRPRQII

SEQ ID NO 7
WFMKKAQEHKRSFTESQLQEGKHVIGLQMGSNRG----------------
-----

SEQ ID NO 6
S

SEQ ID NO 7
-
```

SEQ ID NO 1: sarcomere tropomyosin kappa, TPM1-kappa; NCBI accession: IPI00455050.1

SEQ ID NO 2: sarcomere tropomyosin kappa; NCBI accession: IPI00455050.1

SEQ ID NO 3: beta tropomyosin; NCBI accession: IPI00220709.3

SEQ ID NO 4: TPM1 human tropomyosin 1 alpha-chain; NCBI accession: IPI00014581.1

SEQ ID NO 5: tropomyosin 4; NCBI accession: IPI00010779.3

SEQ ID NO 6: transgelin; NCBI accession: IPI00216138.5

SEQ ID NO 7: transgelin variant; NCBI accession: IPI00216138.5

Figure 1:
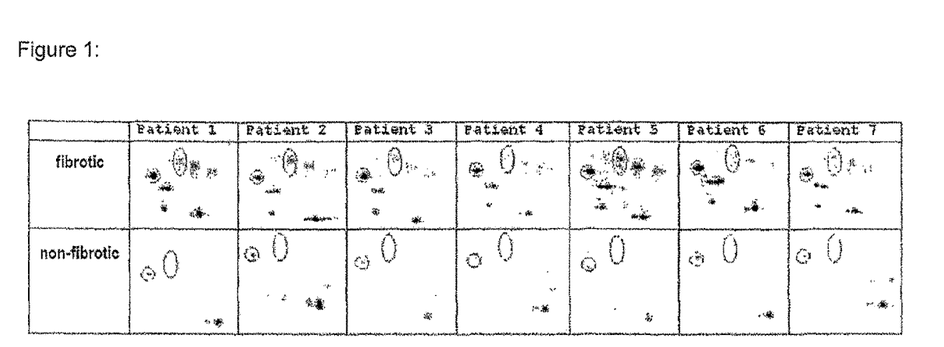
FIG. 1 shows pictures of proteins, separated using 2-D gel electrophoresis, from fibrotic and non-fibrotic cells from cirrhotic liver parenchyma of seven patients who suffered from cirrhosis of the liver connected with hepatitis C.

FIG. 1 shows pictures of the proteins separated using 2-D gel electrophoresis, fibrotic and non-fibrotic cells from cirrhotic liver parenchyma of a total of 7 patients, who suffered from cirrhosis of the liver connected with hepatitis C, having been used. The circular marking shows tropomyosin (beta), and the oval marking shows hMFAP 4. The similarity of the pictures underlines the reproducibility of the results.

In particular, tropomyosin, transgelin, calponin, hMFAP4, and vimentin have been shown to the promising and preferred biomarkers according to the invention. Furthermore, the tropomyosin may be sarcomere tropomyosin kappa, beta tropomyosin, TPM1 human tropomyosin, or tropomyosin 4.

The hMFAP4 cited is the human microfibrillar associated protein 4. In addition to the above-mentioned up-regulated proteins, however, down-regulated metabolic enzymes may also be used as a marker, in particular argininosuccinate synthetase, methylene tetrahydrofolate dehydrogenase, fructose-1,6-biophosphate aldolase, mitochondrial malate dehydrogenase, and mitochondrial acetoacetyl-CoA thiolase.

Some of the identified proteins are discussed briefly hereafter, the explanations provided therein solely being attempts at clarifications which are not to be understood as restrictive in any way in regard to the object for which a patent is sought.

Regucalcin, also known as senescence marker protein-30 (SMP-30), plays a significant role in maintaining the intracellular Ca2+ level by activation of Ca2+ enzymes in the plasma membrane, the microsomes, and the mitochondria. Regucalcin was down-regulated 13-fold in fibrotic liver cells in comparison to healthy liver cells. This may indicate that the compensatory effects of regucalcin were decreased with respect to oxidative stress in diseased liver tissue.

Mitochondrial malate dehydrogenase and mitochondrial acetoacetyl transferase were both down-regulated by 5.9-fold in the fibrotic liver tissue. It was possible to show that the interaction between hepatitis C virus core protein and the proteins NS3 and NS5 with mitochondria resulted in the formation of reactive oxygen species (ROS), which may be an explanation of the weaker expression of the cited enzymes in fibrotic cells.

A further indication of disturbed mitochondrial enzymes in fibrotic liver cells is the decreased expression of the ATP synthase alpha-subunit (ATP5A1), which catalyzes ATP synthesis during oxidative phosphorylation.

Further effects of the hepatitis C virus core protein and the NS5A protein are the association with membranes of the endoplasmatic reticulum, the Golgi apparatus, and an amplification of the intracellular lipid accumulation by interaction with apolipoprotein A1 (apoA1) or A2 (apoA2). The lipid transfer protein is correspondingly inhibited or the synthesis of VLDL (very low density lipoproteins) is disturbed. A significant down-regulation of the acetyl-CoA-acetyltransferase was able to be observed in fibrotic liver cells (fold change: −5.88).

Metabolic disturbances in fibrotic livers also manifest themselves in a decreased expression of glycolytic enzymes such as fructose-1,6-bisphosphate aldolase (fold change: −16.6), enolase-1 (2-phosphodiglycerate hydrolase), or glyoxylase.

Because of these metabolic dysfunctions, the protein synthesis is partially significantly reduced in fibrotic liver cells: serum albumin (fold change: −13.2), which functions as a carrier for fatty acids, steroids, and thyroid hormones and stabilizes the extracellular liquid volume, was only still expressed in a reduced way.

The process of liver regeneration in fibrotic liver cells is apparently impaired by a weaker expression of methylene tetrahydrofolate dehydrogenase (fold change: −9.4), which catalyzes three sequential reactions in the conversion of C-1 derivatives of tetrahydrofolate. A non-reduced enzymatic function is significant for the normal cellular function, growth, and dedifferentiation.

Overall, a disturbance of the cellular equilibrium, the glycolytic reaction pathways, and the lipid compartmentalization and the metabolism appear to exist in fibrotic cells, which encourages the production of reactive organic species (ROS). These in turn induce the synthesis of TGF-β1 in hepatocytes and hepatic stellate cells, the strongest promoters of hepatic fibrogenesis.

The proteins actin alpha (fold change: 6.5) and actin gamma (fold change: 9.1) were able to be identified in the area of the amplified detectable proteins. These are the main components of the thin filaments of muscle cells and the cytoskeleton of non-muscular cells. Actin is apparently a product of the HSC cells and occurs in an amplified way in the event of hepatitis C-induced fibrosis.

A further identified protein is vimentin (fold change: 4.6). This is presumed to be a product of the hepatic stellate cells from the mesenchyma.

Various tropomyosin isoforms, which are apparently not produced by hepatocytes but by myofibroblastic hepatic stellate cells, partially have the highest rates of amplification (fold change: 9.7 to 83.1).

The 34 kDa protein calponin is normally also expressed specifically in smooth muscle cells and binds calmodulin, actin, and tropomyosin. In view of the myofibroblastic activated hepatic stellate cells, calponin was also up-regulated in fibrotic cells according to the results of the proteome analysis (fold change: 18.5).

Transgelin (fold change: 15) is also presumed to be a product of hepatic stellate cells. Transgelin is a 22 kDa protein, which is also referred to as SM22-alpha and has structural similarities to calponin. The amyloid component P, a glycoprotein which is composed of a pair of non-covalently bound pentamers, the subunit having a size from 23 to 25 kDa, was also more strongly expressed in the event of fibrosis than in healthy tissue (fold change: 7.3). The physiological function in hepatic fibrogenesis is unknown up to this point, but the overexpression indicates an abnormal cellular process.

In summary, it may be stated that the overexpression or underexpression of the proteins usable as biomarkers is to be attributed to a disturbed cellular equilibrium, impaired mitochondrial and metabolic enzymes, reduced cellular synthesis, and an amplified expression of cytoskeletal proteins during the process of apoptosis in fibrotic liver cells.

In the study of a sample for the proteins used as the biomarkers, as described above, a procedure may be used in which, with the aid of a 2-D gel electrophoresis, comprising isoelectrical focusing in the first dimension and gel electrophoresis in the second dimension, a separation of the proteins is performed and the overexpression and/or underexpression of specific proteins is proven by comparison of the protein pattern to a non-fibrotic control sample. The gel electrophoresis is preferably an SDS polyacrylamide gel electrophoresis. Corresponding software for analyzing the gels is obtainable, for example, from GE Healthcare in the form of the DeCyder software.

To detect the proteins, the samples are preferably labeled using a pigment before performance of the 2-D gel electrophoresis. The pigments are preferably fluorescent pigments. The use of Cy2, Cy3, and/or Cy5 is especially preferred. These pigments are obtainable, for example, from GE Healthcare, Freiburg, Germany. These are carbomethylindocyanine pigments, two indole molecules being connected via a carbon chain having conjugated double bonds. The corresponding functionalized pigments may be caused to react with the thiol groups of the side chains of the cysteine to link the proteins covalently to the pigments. For the purpose of reduction of disulfide bridges, the sample is first reduced with the aid of a suitable reducing agent, for example, with the aid of tris (2-carboxyethyl) phosphine hydrochloride (TCEP). Subsequently, a reaction is performed with corresponding functionalized pigment until finally the reaction is stopped by adding DTT. However, the functionalization of other amino acid residues with the aid of the pigments is also conceivable, for example, the side chain of lysine.

The use of the Cy3, Cy5 pigment system is particularly advantageous in that, in addition to the actual sample, an internal standard may also be used during the 2-D gel electrophoresis, the actual sample and the internal standard being provided with different pigments (Cy3 and Cy5, respectively).

Of course, in addition to the cited pigments, other (fluorescent) pigments are also usable, which are known from the prior art, such as fluorescein or tetramethyl rhodamine.

The detection and the quantification of the proteins used as the markers may also be performed with the aid of further protein diagnostic methods known to those skilled in the art, in particular employing radioactive or fluorescence-marked antibodies. In particular, bioanalytical methods suitable for this purpose are to be cited here, such as immunohistochemistry, antibody arrays, luminex, ELISA, immunofluorescence, and radio immunoassays. The detection and the quantification of the proteins used as the markers may also be performed using further bioanalytical methods suitable for this purpose, such as mass-spectrometry methods, e.g., MRM (multi-reaction monitoring) or AQUA (absolute quantification), with the aid of which the marker proteins may be quantitatively measured.

The sample used for detecting the proteins may be a sample of liver tissue which was removed with the aid of a biopsy. However, the use of (whole) blood, serum, or plasma samples, which are obviously easier to obtain, is also possible.

In addition to the described method, the invention also relates to the use of the cited proteins as biomarkers for the detection of an inflammation of the liver, in particular of a hepatic fibrosis.

The cited marker proteins according to the invention may also be used in further embodiments for differential diagnosis, in particular differential-diagnostic early recognition, course prognosis of the liver illness, judgment of the degree of severity, course judgment accompanying the treatment, etiology, and in vitro diagnostics.

In a further embodiment, the invention relates to a kit or diagnostic device for performing the method according to the invention, the kit containing at least one biomarker according to the invention (also: marker protein) together with detection reagents and further aids.

The following examples are used to explain the invention without restricting the invention to these examples.

EXAMPLE

Example 1

Sample Analysis

Liver parenchyma was taken from a total of seven patients having a hepatitis C infection, genotype 1, who had been subjected to a liver transplantation, immediately cooled on ice, and stored at −86° C. Sample tissues were separated between fibrotic tissue and healthy sections under the microscope. The fibrotic material was taken along the fibrotic septum. The layers for the 2-D gel electrophoresis were stained using hematoxylin and stored at −20° C. The isolated cells from the microdissection were placed in 100 μL lysis buffer (Iris HCI 30 mM; thiourea 2 M; urea 7 M, CHAPS 4%, pH 8.0) and subsequently broken up by applying ultrasound (6×10 s pulses).

DNA and other cell residues were removed by a centrifugation (12,000 g for five minutes). The protein concentration of the lysate was ascertained.

To prepare an internal standard, 3 mcg of the tissue lysate was reduced by application of 2 nmol tris-(2-carboxyethyl)-phosphine hydrochloride (TCEP) at 37° C. in the dark over a time span of one hour. Cy pigments (GE Healthcare, Freiburg, Germany) were diluted using nonaqueous DMF p.a. (2 nmol/μl) and 4 nmol Cy3 was admixed to the samples reduced with the aid of TCEP. After an incubation time of 30 minutes at 37° C., the labeling reaction was stopped by adding 4 μL DTT (1.08 g/mL).

The cysteine amino acids of the proteins to be studied (3500 fibrotic cells, 2500 non-fibrotic cells) were also reduced by incubation with 2 nmol TCEP at 37° C. in the dark for one hour, before 4 nmol Cy5 was added. After thorough mixing, the samples were reacted for 30 minutes at 37° C. in the dark. The reaction was stopped by adding 10 μL DTT.

To prepare the isoelectric focusing, 10 μl ampholine 2-4 (GE Healthcare) was added. The Cy3-marked and Cy5-marked cells were concurrently processed further after thorough mixing.

Subsequently, a 2-D gel electrophoresis was performed, a 21.25 h voltage gradient being used for the isoelectric focusing. 125 mM tris, 40% (w/v) glycerol, 3% (w/v) SDS, 65 mM DTT, pH 6.8 was used for 10 minutes as an equilibration buffer. Subsequently, a polyacrylamide gel electrophoresis was performed in the second dimension.

With the aid of a suitable scanner (Typhoon 9400, GE Healthcare), images were recorded after completed gel electrophoresis and analyzed with the aid of the ImageQuant software and the DeCyder software (GE Healthcare). In this way, a differential analysis was able to be performed in the gel (DIA), to detect and quantify the individual spots.

The proteins were cleaved at 37° C. overnight with the aid of the enzyme trypsin in 10 mM ammonium bicarbonate buffer (pH 7.8). The fragments generated in this way were extracted twice using an acetonitrile-formic acid mixture for further partitioning and mass-spectrometry study. This was performed with the aid of online-RP-capillary HPLC, coupled with nano-ESI-MS (electrospray ionization mass spectrometry). Complete identification of the protein spots was able to be performed with the aid of the HPLC-MS coupling and employing suitable protein databanks (NCBI, National Center for Biotechnology Information).

Example 2

Protein Tropomyosin and its Detection in Patient Sera

A protein detection using Western blot analysis was performed for this purpose. The tropomyosin protein was able to be identified reproducibly in patient sera of cirrhosis of the liver patients of various origins (FIG. 2).

Figure 2:
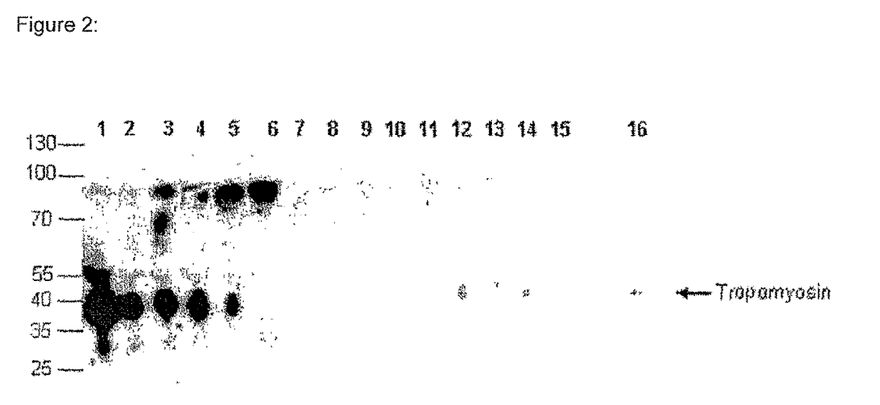
FIG. 2 shows Western blot analysis of tropomyosin in sera of patents having cirrhosis of the liver.

FIG. 2: tropomyosin Western blot of the following patient sera:

1: (patient 1) hepatitis C (HepC) cirrhosis CHILD C
2: (patient 2) HepC cirrhosis CHILD C
3: (patient 3) HepC cirrhosis CHILD C
4: (patient 4) HepC cirrhosis CHILD C
5: (patient 5) HepC cirrhosis CHILD C
6: (patient 6) HepC cirrhosis CHILD A
7: (patient 7) HepC cirrhosis CHILD A
8: (patient 8) normal control
9: (patient 9) normal control
10: (patient 10) normal control
11: (patient 11) normal control
12: (patient 12) ethyl-toxic cirrhosis CHILD C
13: (patient 13) ethyl-toxic cirrhosis CHILD C
14: (patient 14) HepB fibrosis
15: (patient 15) HepC fibrosis
16: tropomyosin 0.005 μg The patients were, on the one hand, patients infected with hepatitis C having cirrhosis of the liver and/or fibrosis, and, on the other hand, patients having ethyl-toxic cirrhosis of the liver and one hepatitis B patient having liver fibrosis. Patients having cirrhosis of the liver were divided further into various CHILD classes, which provide information about the degree of severity of the cirrhosis, by incorporating various blood parameters. The classification is performed from CHILD A having a survival rate of approximately 100% for the next year up to CHILD C having a survival rate of approximately 30%. A tropomyosin band was not able to be detected in patient sera of healthy normal controls (FIG. 2, bands 8-11). Interestingly, tropomyosin was able to be detected in hepatitis C patients having a CHILD C classification (FIG. 2, bands 1-5), while no protein band was detectable in cirrhotics having a CHILD A cirrhosis (FIG. 2, bands 6-7). In addition, ethyl-toxic cirrhosis of the liver were studied (CHILD C classification), which also showed a signal for tropomyosin in attenuated form and had a CHILD C classification (FIG. 2, bands 12-13). Furthermore, a tropomyosin band was able to be detected in the hepatitis B fibrosis patients, which was not possible in the hepatitis C fibrosis patients.

The invention claimed is:

1. A method for the diagnosis of inflammation of the liver, comprising the step of determining the concentration of at least one protein selected from
   (a) the group consisting of ER60, vimentin, actin alpha 1 skeletal muscle protein, hMFAP 4, tropomyosin, PTGES 2, amyloid P-component, transgelin, calponin 1, *Homo sapiens* p20 protein, 17 kDa myosin light chain, H chain H IgG B12, prolyl 4-hydroxylase beta subunit, and
   (b) the group consisting of methylene tetrahydrofolate dehydrogenase 1, PRO2619, aldehyde dehydrogenase 1, fibrinogen alpha-chain preproprotein, fructose-bisphosphate-aldolase B, argininosuccinate synthetase, EEF1A2, ATP5A1, alpha-2-actin, regucalcin, serum albumin, mitochondrial malate dehydrogenase, and mitochondrial acetoacetyl-CoA thiolase,
in a sample from a human patient,
wherein a concentration of said at least one protein in said sample from group (a) which is elevated in relation to the healthy state indicates the presence of an inflammation of the liver; and
wherein a concentration of said at least one protein in said sample from group (b) which is decreased in relation to the healthy state indicates the presence of an inflammation of the liver.

2. The method of claim 1, wherein said inflammation of the liver is hepatic fibrosis or cirrhosis of the liver.

3. The method of claim 1, comprising the steps of
determining the concentration of one or more proteins in a sample from a human, as markers for inflammation of the liver, and
comparing the concentration of said one or more proteins in said sample with the amount of said one or more proteins in the healthy human state,
wherein a concentration of said one or more proteins in said sample which is elevated in relation to the healthy state indicates the presence of an inflammation of the liver, and
wherein said one or more proteins are selected from the group consisting of ER60, vimentin, actin alpha 1 skeletal muscle protein, hMFAP 4, tropomyosin, PTGES 2, amyloid P-component, transgelin, calponin 1, *Homo sapiens* p20 protein, 17 kDa myosin light chain, H chain H IgG B12, and prolyl 4-hydroxylase beta subunit.

4. The method of claim 1, comprising the steps of
determining the concentration of one or more proteins in a sample from a human, as markers for inflammation of the liver, and
comparing the concentration of said one or more proteins in said sample with the amount of said one or more proteins in the healthy human state,
wherein a concentration of said one or more proteins in said sample which is decreased in relation to the healthy state indicates the presence of an inflammation of the liver, and
wherein said one or more proteins are selected from the group consisting of methylene tetrahydrofolate dehydrogenase 1, PRO2619, aldehyde dehydrogenase 1, fibrinogen alpha-chain preproprotein, fructose-bisphosphate-aldolase B, argininosuccinate synthetase, EEF1A2, ATP5A1, alpha-2-actin, regucalcin, serum albumin, mitochondrial malate dehydrogenase, and mitochondrial acetoacetyl-CoA thiolase.

5. The method of claim 4, wherein said inflammation of the liver is hepatic fibrosis.

6. The method according to claim 1, wherein the tropomyosin is sarcomere tropomyosin kappa, beta tropomyosin, TPM 1 human tropomyosin, or tropomyosin 4.

7. The method according to claim 1, wherein determining the concentration of said one or more proteins is performed by immunohistochemistry, antibody arrays, luminex, ELISA, immunofluorescence, or radio immunoassays.

8. The method according to claim 1, wherein determining the concentration of said one or more proteins is performed using mass-spectrometry methods.

9. The method according to claim 1, wherein determining the concentration of said one or more proteins is performed by 2-D electrophoresis, an isoelectric focusing being performed in the first dimension, and a gel electrophoresis being performed in the second dimension.

10. The method according to claim 9, wherein the gel electrophoresis is an SDS-polyacrylamide gel electrophoresis.

11. The method according to claim 9, wherein the sample is labeled using a pigment before performing the 2-D gel electrophoresis.

12. The method according to claim 11, wherein the pigment is Cy2, Cy3, and/or Cy5.

13. The method according to claim 1, wherein the sample is a liver biopsy sample.

14. The method according claim 1, wherein the sample is blood serum, blood plasma, or (whole) blood.

* * * * *